(12) United States Patent
Hosokawa et al.

(10) Patent No.: US 12,297,131 B2
(45) Date of Patent: May 13, 2025

(54) METHOD FOR REMOVING BIOFILM

(71) Applicant: KAO CORPORATION, Tokyo (JP)

(72) Inventors: Kento Hosokawa, Wakayama (JP); Masashi Chiba, Wakayama (JP); Tetsuji Yamamoto, Wakayama (JP); Takanori Tanaka, Wakayama (JP)

(73) Assignee: KAO CORPORATION, Tokyo (JP)

( * ) Notice: Subject to any disclaimer, the term of this patent is extended or adjusted under 35 U.S.C. 154(b) by 811 days.

(21) Appl. No.: 17/604,683

(22) PCT Filed: Apr. 28, 2020

(86) PCT No.: PCT/JP2020/018137
§ 371 (c)(1),
(2) Date: Oct. 18, 2021

(87) PCT Pub. No.: WO2020/230626
PCT Pub. Date: Nov. 19, 2020

(65) Prior Publication Data
US 2022/0212966 A1 Jul. 7, 2022

(30) Foreign Application Priority Data
May 10, 2019 (JP) ................... 2019-089995

(51) Int. Cl.
| C02F 1/50 | (2023.01) |
| C02F 1/70 | (2023.01) |
| C02F 1/72 | (2023.01) |
| C02F 101/20 | (2006.01) |
| C02F 103/02 | (2006.01) |

(52) U.S. Cl.
CPC ............. C02F 1/50 (2013.01); C02F 1/70 (2013.01); C02F 1/722 (2013.01); *C02F 2101/203* (2013.01); *C02F 2101/206* (2013.01); *C02F 2103/023* (2013.01); *C02F 2303/20* (2013.01); *C02F 2305/023* (2013.01); *C02F 2305/026* (2013.01)

(58) Field of Classification Search
CPC .... C02F 1/50; C02F 1/70; C02F 1/722; C02F 2101/203; C02F 2101/206; C02F 2103/023; C02F 2303/20; C02F 2305/023; C02F 2305/026; C02F 2101/20; C02F 1/72; C11D 2111/20; C11D 3/0042; C11D 3/3947; C11D 3/48; A01P 1/00; A61L 2/186; A01N 59/00
See application file for complete search history.

(56) References Cited

U.S. PATENT DOCUMENTS

| 2004/0191913 A1 | 9/2004 | Yoshikawa |
| 2010/0133184 A1 | 6/2010 | Gojo et al. |
| 2011/0159117 A1 | 6/2011 | Mayer et al. |
| 2012/0094887 A1 | 4/2012 | Tanaka et al. |
| 2012/0107415 A1 | 5/2012 | Lisowsky et al. |
| 2012/0279522 A1 | 11/2012 | Varrin, Jr. et al. |
| 2014/0072653 A1 | 3/2014 | Buschmann |
| 2014/0202942 A1 | 7/2014 | McGuire |
| 2016/0120184 A1 | 5/2016 | Gedanken et al. |
| 2016/0200605 A1 | 7/2016 | Safarzdeh-Amiri et al. |
| 2017/0107128 A1 | 4/2017 | Buschmann |
| 2018/0028417 A1 | 2/2018 | Koo et al. |
| 2022/0212966 A1 | 7/2022 | Hosokawa et al. |

FOREIGN PATENT DOCUMENTS

| CN | 1520520 A | 8/2004 |
| CN | 1705735 A | 12/2005 |
| CN | 1958485 A | 5/2007 |
| CN | 101200338 A | 6/2008 |
| CN | 101940905 A | 1/2011 |
| CN | 102811955 A | 12/2012 |
| CN | 105377749 A | 3/2016 |
| CN | 105377752 A | 3/2016 |
| CN | 109320011 A | 2/2019 |
| DE | 10 2007 003 748 A1 | 7/2008 |
| EP | 3 967 144 A1 | 3/2022 |
| JP | 48-10204 B | 4/1973 |
| JP | 50-12848 A | 2/1975 |
| JP | 54-28447 B1 | 9/1979 |
| JP | 56-78695 A | 6/1981 |
| JP | 2004-231671 A | 8/2004 |
| JP | 2004-244345 A | 9/2004 |
| JP | 2005-323561 A | 11/2005 |
| JP | 2012-512199 A | 5/2012 |
| JP | 2013-139953 A | 7/2013 |
| JP | 2015-124361 A | 7/2015 |
| JP | 2016-35009 A | 3/2016 |
| JP | 2016-102227 A | 6/2016 |
| JP | 2017-518432 A | 7/2017 |
| JP | 2018-510136 A | 4/2018 |
| JP | 2018-168097 A | 11/2018 |
| KR | 10-0808373 B1 | 2/2008 |

(Continued)

OTHER PUBLICATIONS

International Search Report for PCT/JP2020/018137 mailed on Jul. 21, 2020.
Extended European Search Report for European Application No. 20805053.4, dated May 4, 2023.
International Preliminary Report on Patentability and English translation of the Written Opinion of the International Searching Authority for International Application No. PCT/JP2020/018137, dated Nov. 25, 2021.
International Preliminary Report on Patentability and English translation of the Written Opinion of the International Searching Authority for International Application No. PCT/JP2020/018139, dated Nov. 25, 2021.

(Continued)

*Primary Examiner* — Thuan D Dang
(74) *Attorney, Agent, or Firm* — Birch, Stewart, Kolasch & Birch, LLP

(57) ABSTRACT

The present invention is a method for removing a biofilm containing a metal and formed in a water system, wherein the biofilm is brought into contact with (a) a compound having a hydroxyl radical generation ability and (b) a reducing agent.

16 Claims, No Drawings

(56) References Cited

FOREIGN PATENT DOCUMENTS

| KR | 10-2009-0119922 A | 11/2009 |
|---|---|---|
| KR | 10-1140217 B1 | 5/2012 |
| WO | WO 2004/035718 A2 | 4/2004 |
| WO | WO 2009/028757 A1 | 3/2009 |
| WO | WO 2010/140581 A1 | 12/2010 |
| WO | WO 2015/125739 A1 | 8/2015 |
| WO | WO 2015/184210 A1 | 12/2015 |
| WO | WO 2020/230626 A1 | 11/2020 |
| WO | WO 2020/230627 A1 | 11/2020 |

OTHER PUBLICATIONS

International Search Report for International Application No. PCT/JP2020/018139, dated Jul. 28, 2020, with an English translation.
Chinese Office Action and Search Report for Chinese Application No. 202080034904.X, dated May 10, 2023, with an English translation.
Extended European Search Report for European Application No. 20806204.2, dated Jun. 1, 2023.
Chinese Office Action and Search Report for Chinese Application No. 202080034904.X, dated Nov. 18, 2022, with an English translation.
Li et al., "Studies of Theoretical Basis and Application of Liquid-Phase Sealing Technology in the Preparation of Functional Ceramic Powders," Shanghai Sciences Puji Press, 1997, p. 201, 3 pages total.
Chinese Office Action and Search Report for Chinese Application No. 202080033854.3, dated Aug. 25, 2022, with English translation.
Christensen et al., "Biofilm Removal by Low Concentrations of Hydrogen Peroxide," Boifouling, vol. 2, 1990, pp. 165-175 (13 pages total).
Japanese Office Action for Japanese Application No. 2020-079177, dated May 7, 2024.
"How to convert percent to ppm," Retrieved from: https://rapidtables.com/convert/number/Percent_to_PPM.html, retrieved on Apr. 3, 2018, 1 page total.
Fenton, "XLI.—The Constitution of a new Dibasic acid, resulting from the Oxidation of Tartaric Acid," Journal of the Chemical Society, Mar. 17, 1896, pp. 546-562.
Khuntia et al., "Quantitative prediction of generation of hydroxyl radicals from ozone microbubbles," Chemical Engineering Research and Design, vol. 98, 2015, pp. 231-239.
Kuppusamy et al. "Characterization of Free Radical Generation by Xanthine Oxidase, Evidence for Hydroxyl Radical Generation," The Journal of Biological Chemistry, vol. 264, No. 17, Jun. 15, 1989, pp. 9880-9884.
Matavos-Aramyan et al., "Cryptosporidium-contaminated water disinfection by a novel Fenton process," Free Radical Biology and Medicine, vol. 106, 2017, pp. 158-167.
Nakamura et al., "Reevaluation of Quantitative ESR Spin Trapping Analysis of Hydroxyl Radical by Applying Sonolysis of Water as a Model System," Bulletin of the Chemical Society of Japan, vol. 83, No. 9, 2010, pp. 1037-1046.
Oh et al., "Stabilization of hydrogen peroxide using tartaric acids in Fenton and fenton-like oxidation," Korean J. Chem. Eng., vol. 33, No. 3, 2016, pp. 885-892.
Pawar et al., "An overview of the Fenton Process for Industrial Wastewater," IOSR Journal of Mechanical and Civil Engineering (IOSR-JMCE), vol. 2, 2016, pp. 127-136.
Pei et al., "Electron Spin Resonance Evidence for Electro-generated Hydroxyl Radicals," Environmental Science & Technology, vol. 54, Sep. 15, 2020, pp. 13333-13343.
Japanese Office Action for Japanese Application No. 2020-079177, dated Oct. 8, 2024.
Lakretz et al., "Biofilm control in water by advanced oxidation process (AOP) pre-treatment: effect of natural organic matter (NOM)," Water Science & Technology, vol. 64, No. 9, 2011, pp. 1876-1884.
Korean Office Action for Korean Application No. 10-2021-7036289, dated Jan. 15, 2025.
Jansson et al., "Iron prevents ascorbic acid (vitamin C) induced hydrogen peroxide accumulation in copper contaminated drinking water," Free Radical Research, vol. 39, No. 11, Nov. 2005, pp. 1233-1239.

METHOD FOR REMOVING BIOFILM

FIELD OF THE INVENTION

The present invention relates to a biofilm removing method for removing a biofilm produced in a water system.

BACKGROUND OF THE INVENTION

A biofilm is also called a microbial film or slime, and generally refers to a structure formed to encapsulate microorganisms such as bacteria or the like in polymeric substances such as polysaccharides, proteins, nucleic acids and the like produced by the microorganisms when the microorganisms adhere to surfaces of substances to grow. The formation of a biofilm causes many kinds of problems due to microorganisms, thus posing problems in various industrial fields. For example, when a biofilm is formed within piping of a food plant, this biofilm peels off to be mixed as a foreign substance into products, to cause the occurrence of food poisoning due to toxins derived from bacteria, or the like. Further, the formation of a biofilm onto metal surfaces causes metal corrosion and accelerates the deterioration of equipment.

Systems utilizing aqueous media, such as cooling systems for plant equipment or buildings using water-cooled cooling towers, cooling pools, or the like have conventionally been used. In such systems, the microbial contamination of water used is problematic. For example, in a cooling system using a water-cooled cooling tower, microorganisms mixed into cooling water form a biofilm inside piping, particularly in a heat exchanger. The biofilm formed in the heat exchanger decreases the efficiency of heat exchange and increases the amount of electricity used in the cooling system. In order to prevent the biofilm from being formed, the periodical replacement and cleaning of water are required, but they increase maintenance costs of the system. While, in equipment, apparatuses or the like using cooling water, such as water-cooled cooling towers or the like, antimicrobial agents or growth inhibitors called slime control agents may sometimes also be added to the cooling water to inhibit a biofilm, treatment using no slime control agents is more desirable from the viewpoint of safety, the corrosion of metal piping, chemical agent costs or the like.

Various kinds of proposals have conventionally been offered as measures against contamination incurred due to microorganisms or the like.

JP-A 2012-512199 discloses that a disinfection/decontamination agent containing vitamin, a metal ion, a surface-active compound and a predetermined antimicrobial active substance can be used for the degradation of biofilms.

JP-A 2016-102227 discloses a method for preventing a biofilm in a cooling water system in which cooling water cooled in a cooling tower is circulated to a heat exchanger and the cooling tower is supplied with supplementary water, wherein water in the cooling water system is treated by removing phosphoric acid in the supplementary water and using a non-phosphoric corrosion inhibitor as a corrosion inhibitor.

JP-A 2016-035009 discloses a biofilm removing agent composition for hard surfaces containing 1 mass % or more and 40 mass % or less of internal olefin sulfonates.

JP-A 2018-168097 discloses a biofilm formation inhibiting composition containing a specific cyclic aldehyde compound and an organic solvent.

JP-A 2017-518432 discloses a method for treating a biofilm-affected surface including the step of contacting the affected surface with a predetermined aqueous alkali surfactant composition having a surfactant hydroxide molarity of from 2 to 9.

SUMMARY OF THE INVENTION

The present invention provides a biofilm removing method capable of effectively removing a biofilm formed in a water system, such as an apparatus, equipment or the like including a member coming in contact with water, such as a cooling tower, bathtub piping or the like.

The present invention relates to a method for removing a biofilm containing a metal and formed in a water system, wherein the biofilm is brought into contact with (a) a compound having a hydroxyl radical generation ability (hereinafter also referred to as component (a)), and (b) a reducing agent (hereinafter also referred to as component (b)).

According to the present invention, provided is a biofilm removing method capable of effectively removing a biofilm formed in a water system.

EMBODIMENTS OF THE INVENTION

An effect development mechanism by a biofilm removing method of the present invention is not necessarily thoroughly understood, but is considered as follows. The present inventors have found that biofilms in water systems can be decomposed or dispersed in water owing to hydroxyl radicals, thereby contributing to the removal of the biofilms from equipment. In terms of the efficiency of the action of the hydroxyl radicals and the biofilms formed in the equipment, the efficiency is poor even if the hydroxyl radicals are present on the surface of the biofilms, and high biofilm removal efficiency can be expected if the hydroxyl radicals can be produced widely inside the biofilms formed in the equipment. As all components (a) and (b), and further (c), of the present invention are small molecules, they are easy to move widely inside the biofilms formed in the equipment. It has been found that, in biofilms produced in water systems, metal ions originating for example in materials of equipment or water supplied to the water systems are insolubilized to water and accumulated as salts, oxides or the like. A reducing agent (component (b)) approaches these accumulated metal ions to react with them, thereby forming reduced metal ions (for example, $Fe^{3+} \rightarrow Fe^{2+}$). Further, it is considered that these reduced metal ions and a compound having a hydroxyl radical generation ability (component (a)) assumed to be present nearby cause Fenton-like reactions, thereby generating hydroxyl radicals, which decompose the biofilms or tear them into pieces small enough to be dispersed in water. It is considered that, as metal ions oxidized due to the Fenton-like reactions are further reduced by component (b) to continuously cause Fenton-like reactions with component (a), the effect of removing biofilms is sustainably developed. Moreover, it is considered that a higher biofilm removal effect is developed when an organic acid of a specific structure (component (c)) is used, as component (c) forms complexes with the insolubilized metal ions present within the biofilms to make the metals more likely to be solubilized to water, and as a result, the metal ions can be present in a more uniform manner within the biofilms, which accelerates the reduction of the metal ions due to component (b), as well as the generation of hydroxyl radicals from component (a).

As mentioned above, it is considered that an efficient biofilm removal effect is obtained by the biofilm removing method of the present invention, as trace amounts of metal ions accumulated within the biofilms are utilized to continuously generate hydroxyl radicals in a wide range of places in the biofilms. Note that a comparative example explained later shows that even if a metal ion is used together with components (a) and (b) and brought into contact with a biofilm containing no metal ions, the biofilm cannot be removed. From this fact, it is inferred that, in order to obtain the effect of the present invention, components (a) and (b) need to act, while coexisting with each other, on biofilms in which metal ions are present.

Note that effects of the present invention are not limited to the aforementioned acting mechanism.

[Component (a)]

Component (a) is a compound having a hydroxyl radical generation ability.

Examples of component (a) include a compound generating a hydroxyl radical through a Fenton-like reaction.

Examples of component (a) include one or more compounds selected from hydrogen peroxide, percarbonate salts and organic peracids, and one or more compounds selected from hydrogen peroxide and percarbonate salts are preferable from the viewpoints of availability, economy and the hydroxyl radical generation ability. Examples of the percarbonate salts include alkali metal percarbonate salts such as sodium percarbonate, potassium percarbonate and the like, and sodium percarbonate is preferable from the viewpoints of availability, economy and the hydroxyl radical generation ability.

In the present invention, "Fenton-like reactions" can refer to the Fenton reaction and hydroxyl radical generation reactions due to reactions of hydrogen peroxide with metal species other than an iron ion (conveniently referred to as pseudo-Fenton reactions). That is, in the present invention, "Fenton-like reactions" may be a concept encompassing the Fenton reaction caused by an iron ion, and quasi-Fenton reactions, i.e., hydroxyl radical generation reactions caused by metal species other than an iron ion. Pseudo-Fenton reactions may be chemical reactions through which hydroxyl radicals are produced from compounds generating hydroxyl radicals with metal ions other than an iron ion as catalysts.

The Fenton reaction is defined as a chemical reaction through which hydroxyl radicals are produced from hydrogen peroxide with iron(II) as a catalyst.

On the other hand, pseudo-Fenton reactions are reactions caused by using as metal species, metal species known to cause reactions similar to those caused by iron(II), or metal species selected from the transition elements in the fourth period of the periodic table found by the present invention (scandium, titanium, vanadium, chromium, manganese, cobalt, nickel and copper), and using as compounds generating hydroxyl radicals, compounds known to cause reactions similar to those caused by hydrogen peroxide with the metal species, or compounds selected from hydrogen peroxide, percarbonate salts and organic peracids found by the present invention.

[Component (b)]

Component (b) is a reducing agent.

Component (b) may be a compound acting as a reducer for metals, for example, iron. Note that metals for which component (b) of the present invention acts as a reducer represent metals in a reducible state.

Examples of component (b) include one or more compounds selected from:

(b-1) compounds with an enediol structure: for example, ascorbic acid or salts thereof, vitamin C extracted from natural products, tannic acid, erythorbic acid or salts thereof;

(b-2) hydroxylamines: for example, N,N-diethylhydroxylamine;

(b-3) phenolic reducing agents: for example, gallic acid, methylhydroquinone, dimethylhydroquinone, trimethylhydroquinone, t-butylhydroquinone, methoxyhydroquinone, chlorohydroquinone; and (b-4) other reducing agents: ascorbic acid derivatives or salts thereof, hydrosulfites, pyrosulfites, sulfites, hydrogensulfites, thiosulfates, thioureadioxide. Examples of salts of these compounds include salts of alkali metals such as sodium, potassium and the like and alkaline earth metal salts such as calcium salts and the like.

Component (b) is preferably ascorbic acid or salts thereof and vitamin C extracted from natural products, and more preferably ascorbic acid or salts thereof from the viewpoints of availability and enhancing the effect of removing biofilms (hereinafter also referred to as biofilm removal properties).

[Component (c)]

In the present invention, components (a) and (b) are preferably brought into contact with the biofilm together with (c) a monovalent or divalent organic acid or a salt thereof with a primary dissociation constant (hereinafter referred to as pKa1) of 1.2 or more and 4.6 or less (component (c)) from the viewpoint of further enhancing the effect of removing biofilms. Of such organic acids or salts thereof, compounds acting as reducers are treated as component (b).

The pKa1 of component (c) is preferably 1.8 or more and more preferably 2.5 or more, and preferably 3.9 or less and more preferably 3.3 or less from the viewpoint of biofilm removal properties.

The molecular weight of the organic acid of component (c) may be, for example, 70 or more, further 75 or more and further 95 or more, and 200 or less, further 180 or less, further 165 or less and further 160 or less from the viewpoint of biofilm removal properties. The organic acid of component (c) has preferably 2 or more, and preferably 8 or less, more preferably 6 or less and further preferably 4 or less carbons from the viewpoint of biofilm removal properties. The organic acid of component (c) is preferably a carboxylic acid and more preferably a monocarboxylic acid or a dicarboxylic acid from the viewpoint of biofilm removal properties.

Examples of component (c) include one or more organic acids or salts thereof selected from hydroxymonocarboxylic acids with 2 or 3 carbons and a molecular weight of 70 or more and 200 or less and further 180 or less, dicarboxylic acids with 3 or 4 carbons and a molecular weight of 70 or more and 200 or less and further 180 or less, hydroxycarboxylic acids with 5 or more and 8 or less carbons and a molecular weight of 70 or more and 200 or less, and salts thereof.

Examples of the hydroxymonocarboxylic acids with 2 or 3 carbons and a molecular weight of 70 or more and 200 or less include glycolic acid (pKa1: 3.83, Mw: 76.1), lactic acid (pKa1: 3.86, Mw: 90.1) and 3-hydoxypropionic acid (pKa1: 4.5, Mw: 90.1).

Examples of the dicarboxylic acids with 3 or 4 carbons and a molecular weight of 70 or more and 200 or less include tartaric acid (pKa1: 2.98, Mw: 150.1), fumaric acid (pKa1: 3.02, Mw: 116.1), maleic acid (pKa1: 1.92, Mw: 116.1), malic acid (pKa1: 3.4, Mw: 134.1), succinic acid (pKa1: 4.19, Mw: 118.1) and malonic acid (pKa1: 2.9, Mw: 104.1).

Examples of the hydroxycarboxylic acids with 5 or more and 8 or less carbons and a molecular weight of 70 or more and 200 or less include gluconic acid (pKa1: 3.86, Mw: 196).

Component (c) is preferably one or more organic acids or salts thereof selected from malonic acid, malic acid, 3-hydroxypropionic acid, succinic acid, lactic acid, tartaric acid, glycolic acid, maleic acid, fumaric acid, gluconic acid and salts thereof from the viewpoint of biofilm removal properties.

Component (c) is more preferably one or more organic acids or salts thereof selected from tartaric acid, fumaric acid, maleic acid, gluconic acid and salts thereof from the viewpoint of biofilm removal properties.

Examples of the salt of the organic acid of component (c) include salts of alkali metals such as sodium, potassium and the like and salts of alkaline earth metals such as calcium and the like.

[Method for Removing Biofilm]

In a biofilm removing method of the present invention, components (a) and (b), and further, component (c) as necessary, are brought into contact with a biofilm containing a metal and formed in a water system. In the present invention, the biofilm is preferably brought into contact with a liquid composition containing component (a), component (b) and water. The liquid composition preferably further contains component (C).

From the viewpoint of biofilm removal properties, the concentration of component (a) in the liquid composition can be set by selecting the upper limit and the lower limit, for example, from 50 ppm or more, further 60 ppm or more and further 80 ppm or more, and 50000 ppm or less, further 30000 ppm or less, further 10000 ppm or less, further 5000 ppm or less, further 3000 ppm or less, further 1000 ppm or less, further 600 ppm or less and further 500 ppm or less, and combining them.

From the viewpoint of biofilm removal properties, the concentration of component (b) in the liquid composition can be set by selecting the upper limit and the lower limit, for example, from 50 ppm or more, further 60 ppm or more and further 80 ppm or more, and 5000 ppm or less, further 3000 ppm or less, further 1000 ppm or less, further 600 ppm or less and further 500 ppm or less, and combining them.

If component (c) is used, from the viewpoint of biofilm removal properties, the concentration of component (c) in the liquid composition can be set by selecting the upper limit and the lower limit, for example, from 50 ppm or more, further 60 ppm or more and further 80 ppm or more, and 5000 ppm or less, further 3000 ppm or less, further 1000 ppm or less, further 600 ppm or less and further 500 ppm or less, and combining them.

In the present invention, components (a) and (b) are preferably brought into contact at a mass ratio of component (a)/component (b) of 0.01 or more and further 0.1 or more, and 100 or less, further 10 or less, further 9.5 or less, further 4.5 or less, further 1.5 or less and further 0.5 or less from the viewpoint of biofilm removal properties.

When the liquid composition is used, the mass ratio of the concentration of component (a) to that of component (b), (a)/(b), in the composition is preferably 0.01 or more and more preferably 0.1 or more, and preferably 100 or less, more preferably 10 or less, further preferably 9.5 or less, furthermore preferably 4.5 or less, furthermore preferably 1.5 or less and furthermore preferably 0.5 or less from the viewpoint of biofilm removal properties.

In the present invention, components (a) and (c) are preferably brought into contact at a mass ratio of component (a)/component (c) of 0.01 or more and further 0.1 or more, and 100 or less and further 10 or less from the viewpoint of biofilm removal properties.

When the liquid composition is used, the mass ratio of the concentration of component (a) to that of component (c), (a)/(c), in the composition is preferably 0.01 or more and more preferably 0.1 or more, and preferably 100 or less and more preferably 10 or less from the viewpoint of biofilm removal properties.

In the present invention, components (b) and (c) are preferably brought into contact at a mass ratio of component (b)/component (c) of 0.01 or more and further 0.1 or more, and 100 or less and further 10 or less from the viewpoint of biofilm removal properties.

When the liquid composition is used, the mass ratio of the concentration of component (b) to that of component (c), (b)/(c), in the composition is preferably 0.01 or more and more preferably 0.1 or more, and preferably 100 or less and more preferably 10 or less from the viewpoint of biofilm removal properties.

In the present invention, an excellent biofilm removal effect is exhibited even if small amounts of surfactants are brought into contact with the biofilm. The concentration of surfactants in the liquid composition may be, for example, less than 100 ppm, further 50 ppm or less, further 10 ppm or less and further 0 ppm from the viewpoints of equipment management without problems such as cavitation caused by bubbles and the like, economy, and satisfactory biofilm removal properties. The liquid composition may be substantially free of surfactants. Here, being substantially free of surfactants may mean that the concentration of surfactants falls within the aforementioned range.

The liquid composition may be a composition not containing or substantially free of metal ions involved in Fenton-like reactions, specifically, ions of metals selected from iron, scandium, titanium, vanadium, chromium, manganese, cobalt, nickel and copper, and further, metal ions. Here, being substantially free of the metal ions may mean a state in which even if the metal ions are contained, the amount thereof is so extremely small that Fenton-like reactions do not sufficiently occur.

In the present invention, components (a) and (b) can be brought into contact at a pH of 2.0 or more, further 2.5 or more, further 3.0 or more and further 3.5 or more, for example, from the viewpoint of preventing materials of equipment from being damaged, and 10.0 or less, further 8.0 or less, further 7.5 or less and further 6.5 or less from the viewpoint of the effect of removing biofilms. That is, the present invention may be a method in which the biofilm is brought into contact with components (a) and (b) under a condition of a pH of 2.0 or more, further 2.5 or more and further 3.0 or more, and 10.0 or less, further 8.0 or less, further 7.5 or less and further 6.5 or less.

When the liquid composition is used, the composition may have a pH of 2.0 or more, further 2.5 or more, further 3.0 or more and further 3.5 or more, and 10.0 or less, further 8.0 or less, further 7.5 or less and further 6.5 or less from the same viewpoint.

A biofilm formed in a water system to be removed by the present invention contains metals within the biofilm formed. The metals contained in the biofilm preferably react with components (a) and (b) to generate hydroxyl radicals. Examples of such metals include, but are not particularly limited to, one or more metals selected from the transition elements in the fourth period of the periodic table, for example, scandium, titanium, vanadium, chromium, manganese, iron, cobalt, nickel and copper, and one or more metals selected from iron, manganese, nickel and copper are preferable from the viewpoint of efficiently producing hydroxyl radicals. Tap water, well water or the like is used as water flowing, circulating and stagnating in the water system, and in the water, while microorganisms such as *Pseudomonas aeruginosa* and the like are contained, metal ions are present concurrently therewith, which are dissolved in trace amounts from the natural world or materials of equipment such as metallic piping or tanks or the like constituting the water system. It is considered that these microorganisms form a biofilm together with water in which metals are dissolved and compounds such as saccharides, proteins and the like produced by the microorganisms, and the biofilm formed further incorporates new metals from water in the system, resulting in the biofilm containing the metals. While the metals are considered to be present as ions in water, they are considered to form salts or oxides with the compounds discharged from the microorganisms to be accumulated in the biofilm.

Constituting materials of water systems often include metals such as iron and the like from the viewpoint of availability at material selection in piping installation or the like, and the metals may be incorporated from the constituting materials into the biofilm formed in the water systems. Thus, the biofilm to which the present invention is directed may contain iron.

The biofilm to which the present invention is directed contains, per mg of the biofilm in a wet state, metals in an amount of preferably 0.5 ng or more, more preferably 1.5 ng or more and further preferably 5 ng or more from the viewpoint of biofilm removal properties, and the upper limit thereof is preferably 50000 ng or less, more preferably 20000 ng or less and further preferably 10000 ng or less from the viewpoint of efficiently promoting the reactions without causing unnecessarily drastic Fenton-like reactions, but is not particularly limited thereto as long as it is the amount accumulable in the biofilm. The amount of metals in the biofilm can be measured by a method described later in Examples.

Water systems to which the present invention is directed are not particularly limited as long as there occurs contact with aqueous liquids in the systems, but refer to, for example, systems that function by flowing or retaining aqueous liquids, and may be apparatuses composed by including members coming in contact with water, such as piping, tanks, pools and the like, installations including the same, and the like. The water may be, in addition to water itself, aqueous media including water and other substances. One example of the water systems is a cooling system provided with a water-cooled cooling tower. In addition, other examples of the water systems may include water flow paths such as plumbing, for example, hot water piping selected from hot water piping of boilers and hot water piping of circulation hot water supply pipes to which hot water is supplied from hot water storage tanks. Moreover, the water systems may include water storage tanks. Further, other examples of the water systems include industrial cooling pools, industrial water supply, water storage or drainage paths, wastewater treatment installations, hot water flow-through heating systems, tanks, pools, bathhouses, filtration installations, paper-making machines in paper mills, tanks and water circulation paths in aquariums, ultrapure water apparatuses, aquaculture installations, plant factories and the like.

The present invention removes a biofilm containing a metal and formed in a water system. Particularly, the present invention removes a biofilm containing a metal and formed in a portion of the water system coming in contact with water.

The water system to which the present invention is directed is preferably provided with a mechanism in which contact with water occurs, for example, a mechanism for periodically flowing water or a mechanism for circulating water. In that case, the biofilm produced in the water system can be removed by adding components (a) and (b), and component (c) as necessary, of the present invention to water to be brought into contact therewith and operating the water system to bring the water into contact therewith, thereby bringing components (a) and (b), and component (c) as necessary, into contact with the biofilm.

The biofilm is brought into contact with components (a) and (b) for a time period of, for example, 3 minutes or more, further 5 minutes or more, further 10 minutes or more and further 30 minutes or more, and 48 hours or less and further 30 hours or less from the viewpoints of the workability and simplicity of equipment management. When the liquid composition is used, the contact time of the liquid composition with the biofilm may fall within this range.

In addition, the biofilm is brought into contact with components (a) and (b) at a temperature of, for example, 5° C. or more and further 10° C. or more, and 85° C. or less and further 60° C. or less. When the liquid composition is used, the temperature of the liquid composition may fall within this range.

At the time of applying components (a) and (b), and component (c) as necessary, of the present invention to the water system, a composition produced in advance to contain these components at concentrations suitable for the contact may be used, or a composition produced to contain these components at high concentrations may be used by diluting in water, or components (a) and (b), and component (c) as necessary, may be used by dissolving in water flowing, circulating or stagnating in the water system separately or after premixing or previously dissolving. The pH may be adjusted as necessary. While components (a), (b) and (c) can be supplied in the form of liquids, solids, aqueous solutions or the like depending on compounds, when the liquid composition is used, the composition is preferably produced immediately before applied to the water system from the viewpoint of the liquid stability of the composition. Further, it is also preferable that components (a) and (b), and component (c) as necessary, of the present invention be brought into contact with the biofilm by dissolving in water flowing, circulating or stagnating in the water system.

The biofilm removing method of the present invention may include bringing the biofilm formed in the water system into contact with a composition containing a metal and preferably one or more metals selected from iron, manganese, nickel and copper to form a biofilm containing a metal or a biofilm with the content of a metal increased, and thereafter bringing it into contact with components (a) and (b). Specifically, the biofilm formed in the water system can be brought into contact with components (a) and (b) after brought into contact with a composition containing one or more metals selected from iron, manganese, nickel and copper, and further, an aqueous composition containing the metals at a concentration of for example 1 ppm or more and 100 ppm or less, for example, by flowing, circulating or stagnating the composition in the water system for a predetermined period, for example, for 3 minutes or more, preferably for 5 minutes or more, more preferably for 10 minutes or more, further preferably for 30 minutes or more, furthermore preferably for an hour or more and furthermore preferably for 2 hours or more, and for a period of for example within 3 days from the viewpoint of workability, and as necessary, thereafter replacing the composition by water containing only a trace amount of metal, such as ordinary tap water, well water or the like, and flowing, circulating or stagnating the water in the water system for a predetermined period. It is considered that, by bringing the biofilm into contact with a composition containing a metal ion at a concentration higher than in ordinary tap water, well water or the like before bringing it into contact with components (a) and (b), more metal can be accumulated within the biofilm, resulting in a further improvement of the effect of removing biofilms.

Note that the effect of the present invention is not developed even if a metal is brought into contact with the biofilm concurrently with components (a) and (b). In this case, the effect of the present invention is not developed even if the metal is brought into contact at a concentration higher than that in ordinary tap water, well water or the like. It is considered that this is because Fenton-like reactions explosively occur at a time in water, thereby making it impossible to act on or decompose the biofilm so that the effect of removing biofilms cannot be developed. Accordingly, in the present invention, it is inferred that a superior effect is exhibited due to Fenton-like reactions occurring inside the biofilm, and if water is used when the biofilm is brought into contact with components (a) and (b), the water desirably contains metal ions involved in the Fenton-like reactions at a concentration as low as possible.

In the method of the present invention, the liquid composition is brought into contact with the biofilm, for example, by dissolving in water flowing, circulating or stagnating in the water system. At that time, external force may be applied. In a portion which cannot directly be touched by hand, such as the inside of plumbing or the like, the biofilm can sufficiently be removed by flow, circulation or the like of the liquid composition to bring it into contact with the biofilm. On the other hand, in a portion which can directly be touched by hand, such as pools, bathhouses or the like, while the biofilm can be removed by only dissolving the liquid composition in water stagnating or the like to bring it into contact with the biofilm, the biofilm can further surely be removed by applying light external force, such as rubbing with a mop, a wiping cloth or the like, etc.

EXAMPLES

Example 1 and Comparative Example 1

Liquid compositions to be brought into contact with a water system were prepared by using components shown in Table 1 and subjected to the following test. The results are shown in Table 1. Note that after the pH of each composition in Table 1 was adjusted by using 10 mM acetate buffer (when adjusting the pH to 4.0) or 10 mM phosphate buffer (when adjusting the pH to 7.0), the concentration of each component was adjusted to a predetermined value. In addition, the balance of each composition in Table 1 is water.

[Biofilm Removal Test (Cooling Tower Model)]

(1) Production of Biofilm

For biofilm production, a water system model was used with an annular reactor (manufactured by Art Kagaku Co., Ltd.) having a culture vessel with a capacity of 100 mL. The culture vessel of the annular reactor was equipped with a cylindrical rotator rotating at a rate of 160 revolutions per minute, and a test piece (SUS304) was attached to this rotator in advance. Cooling water collected from a water-cooled cooling tower for cooling a reaction tank equipment in a chemical plant was supplied to the culture vessel of the annular reactor (maintained at 30° C.), and culture was carried out for 3 weeks to form a biofilm on the test piece.

(2) Measurement of Metal Amount in Biofilm

From the biofilm formed in (1), a sample amount of the biofilm was taken in a wet state with moisture on the surface thereof removed by filter paper, metals were extracted therefrom by using phosphate-buffered saline, the amounts of the metals were measured by ICP-MS, and then, the amounts of the metals contained in 1 mg of the biofilm in the wet state were calculated.

As a result, it was confirmed that this biofilm contained 68 ng/mg of Fe, 4.6 ng/mg of Ni and 3.7 ng/mg of Cu.

(3) Biofilm Removal Test

The test piece on which the biofilm was formed was immersed in 5 mL of each liquid composition containing components in Table 1 at concentrations in Table 1 or a control (ultra-pure water) added into each well of a 6-well plate, and shake was carried out at 30° C. and 60 rpm for 16 hours. Each test piece was dyed with 0.1% crystal violet and thereafter cleaned with ultra-pure water, and the dye was extracted using 1 mL of ethanol to measure the absorbance (OD570). On the basis of the measured OD570, a biofilm removal rate was measured in accordance with the following formula. Note that a blank represents the OD570 of ethanol.

Biofilm removal rate (%)={(control OD570−blank OD570)−(OD570 of example or comparative example−blank OD570)}×100/(control OD570−blank OD570)

Note that the larger a value of the biofilm removal rate in the present test is, the higher the effect is, and a difference of 5% in the biofilm removal rate in the present test can be recognized as a significant difference and a difference of 10% as a clearer difference.

TABLE 1

|  |  |  |  | Example | | | | | | | Comparative example | |
| --- | --- | --- | --- | --- | --- | --- | --- | --- | --- | --- | --- | --- |
|  |  |  |  | 1-1 | 1-2 | 1-3 | 1-4 | 1-5 | 1-6 | 1-7 | 1-1 | 1-2 |
| Liquid composition | Concentration (ppm) | (a) | Hydrogen peroxide | 1000 | 500 | 100 | 100 | 100 | 100 | 100 | 1000 |  |
|  |  | (b) | Sodium ascorbate | 1000 | 500 | 100 | 100 | 100 | 100 | 100 |  | 1000 |
|  |  | (c) | Tartaric acid |  |  |  | 100 |  |  |  |  |  |
|  |  |  | Fumaric acid |  |  |  |  | 100 |  |  |  |  |
|  |  |  | Maleic acid |  |  |  |  |  | 100 |  |  |  |
|  |  |  | Gluconic acid |  |  |  |  |  |  | 100 |  |  |
|  | pH (20° C.) |  |  | 7.0 | 7.0 | 4.0 | 4.0 | 4.0 | 4.0 | 4.0 | 7.0 | 7.0 |
|  | Biofilm removal rate (%) |  |  | 78.8 | 73.9 | 33.8 | 69.2 | 66.5 | 72.8 | 69.5 | 25.4 | 25.3 |

When external force is utilized to remove the biofilm, for example, in such a case that the biofilm is removed by cleaning by rubbing with a mop, a wiping cloth or the like, a biofilm removal rate of 33% or more in this evaluation is sufficient for the development of the effect. When external force is smaller, for example, in the case of removing the biofilm by flow, circulation or the like of the compositions in Table 1, a biofilm removal rate of 40% or more can be sufficient for the removal of the biofilm, and this rate is more preferable.

Example 2 and Comparative Example 2

Liquid compositions to be brought into contact with a water system were prepared by using components shown in Table 2 and subjected to the following test. The results are shown in Table 2. Note that after the pH of each composition in Table 2 was adjusted by using 10 mM acetate buffer or 10 mM phosphate buffer, the concentration of each component was adjusted to a predetermined value. In addition, the balance of each composition in Table 2 is water.

[Biofilm Removal Test (Bathtub Piping Model)]

(1) Production of Biofilm

For biofilm production, a water system model was used with an annular reactor (manufactured by Art Kagaku Co., Ltd.) having a culture vessel with a capacity of 100 mL. The culture vessel of the annular reactor was equipped with a cylindrical rotator rotating at a rate of 160 revolutions per minute, and a test piece (SUS304) was attached to this rotator in advance. While bathtub water collected from a circulation-type bathtub was supplied to the culture vessel of the annular reactor (maintained at 40° C.), R2A agar was added to the supplied water so that the concentration increased by 10 ppm every day as contamination load treatment, and culture was carried out for a week to form a biofilm on the test piece.

(2) Measurement of Metal Amount in Biofilm

The amounts of metals contained in the biofilm formed in (1) were calculated in the same manner as in example 1.

As a result, it was confirmed that this biofilm contained 220 ng/mg of Fe and 6.8 ng/mg of Mn.

(3) Biofilm Removal Test

The test piece on which the biofilm was formed was immersed in 5 mL of each liquid composition containing components in Table 2 at concentrations in Table 2 or a control (ultra-pure water) added into each well of a 6-well plate, and shake was carried out at 40° C. and 60 rpm for 30 minutes. Each test piece was dyed with 0.1% crystal violet and thereafter cleaned with ultra-pure water, and the dye was extracted using 1 mL of ethanol to measure the absorbance (OD570). On the basis of the measured OD570, a biofilm removal rate was measured in accordance with the following formula. Note that a blank represents the OD570 of ethanol.

Biofilm removal rate (%)={(control OD570−blank OD570)−(OD570 of example or comparative example−blank OD570)}×100/(control OD570−blank OD570)

TABLE 2

|  |  |  |  | Example | | | Comparative example | |
|---|---|---|---|---|---|---|---|---|
|  |  |  |  | 2-1 | 2-2 | 2-3 | 2-1 | 2-2 |
| Liquid composition (ppm) | Concentration | (a) | Sodium percarbonate | 1000 | 1000 | 500 | 1000 | |
|  |  | (b) | Ascorbic acid | 1000 | 1000 | 500 |  | 1000 |
|  |  | (c) | Tartaric acid |  | 1000 | 500 |  |  |
|  | pH |  |  | 9.8 | 4.0 | 4.0 | 10.7 | 3.2 |
| Biofilm removal rate (%) |  |  |  | 55.0 | 77.0 | 69.0 | 19.0 | 6.0 |

Example 3 and Comparative Example 3

The biofilm removal rates were measured in the same manner as in example 1 by using test pieces on which the biofilms produced in examples 1 and 2 were formed.

Further, a biofilm removal rate against a biofilm generated due to *Pseudomonas aeruginosa* or that generated due to bacteria of the genus *Sphingomonas* was measured in the following manner.

The results are shown in Table 3.

(1) Production of Biofilm (*Pseudomonas aeruginosa*)

The shaking culture of *Pseudomonas aeruginosa* PAO1 strain (ATCC 15692) was carried out on R2A agar at 30° C. for 16 hours. The resultant culture solution was diluted with R2A agar to 1/100, and 200 μL of the dilution was added to each well of a 96-well microplate to carry out culture at 30° C. for three days to produce a biofilm.

(2) Production of Biofilm (Bacteria of the Genus *Sphingomonas*)

The shaking culture of Bacteria of the genus *Sphingomonas* isolated from cooling water of a cooling tower was carried out on R2A agar at 30° C. for 16 hours. The resultant culture solution was diluted to 1/100 with R2A agar containing 0.1 μM of Iron(III) chloride, 100 μM of manganese (II) chloride, 100 μM of nickel(II) chloride or 100 μM of copper(II) chloride, and 200 μL of the dilution was added to each well of a 96-well microplate to carry out culture at 30° C. for three days to produce a biofilm.

(3) Measurement of Metal Amount in Biofilm

The amounts of metals contained in the biofilms formed in (1) and (2) were calculated in the same manner as in example 1.

As a result, it was confirmed that the biofilm of (1) contained no metals, and the biofilms of (2) contained 19.8 ng/mg of Fe, 7.8 ng/mg of Mn, 1.8 ng/mg of Ni and 12.9 ng/mg of Cu, respectively.

(4) Biofilm Removal Test

Each culture solution in the well was replaced by each liquid composition containing components in Table 3 at concentrations in Table 3 or a control (ultra-pure water) to allow the composition or the water to act thereon at 30° C. for 16 hours. After that, the liquid composition or ultra-pure water was discarded, each well was dyed with 0.1% crystal violet and thereafter cleaned with ultra-pure water twice, 200 μL of ethanol was added thereto, and the absorbance (OD570) was measured. On the basis of the measured OD570, the biofilm removal rate was measured in accordance with the following formula. Note that a blank represents the OD570 of ethanol.

Biofilm removal rate (%)={(control OD570−blank OD570)−(OD570 of example or comparative example−blank OD570)}×100/(control OD570−blank OD570)

TABLE 3

|  |  |  |  | Example 3-1 | Example 3-2 | Example 3-3 | Example 3-4 | Example 3-5 | Example 3-6 | Comparative example 3-1 | Comparative example 3-2 |
|---|---|---|---|---|---|---|---|---|---|---|---|
| Liquid composition | Concentration (ppm) | (a) | Hydrogen peroxide | 500 | 500 | 500 | 500 | 500 | 500 | 500 | 500 |
|  |  | (b) | Sodium ascorbate | 1000 | 1000 | 1000 | 1000 | 1000 | 1000 | 1000 | 1000 |
|  |  |  | $FeCl_3$ |  |  |  |  |  |  | 15 |  |
|  | pH |  |  | 7.0 | 7.0 | 7.0 | 7.0 | 7.0 | 7.0 | 7.0 | 7.0 |
| Origin of biofilm |  |  |  | Cooling tower model (Example 1) | Bathtub piping model (Example 2) | Bacteria of the genus *Sphingomonas* (Example 3) | Bacteria of the genus *Sphingomonas* (Example 3) | Bacteria of the genus *Sphingomonas* (Example 3) | Bacteria of the genus *Sphingomonas* (Example 3) | *Pseudomonas aeruginosa* (Example 3) | *Pseudomonas aeruginosa* (Example 3) |
| Metal amount in biofilm (ng/mg) | Mn |  |  | — | 6.8 | — | 7.8 | — | — | — | — |
|  | Fe |  |  | 68 | 220 | 19.8 | — | — | — | — | — |
|  | Ni |  |  | 4.6 | — | — | — | 1.8 | — | — | — |
|  | Cu |  |  | 3.7 | — | — | — | — | 12.9 | — | — |
| Biofilm removal rate (%) |  |  |  | 79.8 | 83.1 | 53.9 | 42.1 | 42.3 | 75.9 | 0 | 0 |

It can be seen from examples 3-1, 3-2 and 3-3 shown in Table 3 that when a liquid composition containing components (a) and (b) is brought into contact with biofilms containing metals, the biofilm removal rate is very high and the biofilm can be favorably removed. On the other hand, it can be seen from comparative example 3-1 that even if a liquid composition is brought into contact with a biofilm containing no metals, the biofilm cannot be removed. In addition, it can be seen from comparative example 3-2 that even if a liquid composition is brought into contact with a biofilm containing no metals in the presence of a metal (Fe) therein, the biofilm cannot be removed.

Example 4

A liquid composition to be brought into contact with a water system was prepared by using components shown in Table 4 and subjected to the following test. The results are shown in Table 4.

(1) Production of Biofilm (Bacteria of the Genus *Sphingomonas*)

For production, the biofilm producing method in (2) in example 3 was carried out without adding the metals.

(2) Measurement of Metal Amount in Biofilm

The amounts of metals contained in the biofilm formed in (1) were calculated in the same manner as in example 1.

As a result, the biofilm of (1) contained no metals.

(3) Biofilm Removal Test

The culture solution in the well was replaced by a solution in which iron(III) chloride was dissolved at 1.6 ppm in ultra-pure water, and it was left to stand for a minute, 5 minutes, 10 minutes, 30 minutes or 120 minutes and thereafter replaced by phosphate-buffered saline, with which the residual iron(III) chloride solution was cleaned. After that, the liquid composition in Table 4 was prepared by using 10 mM phosphate buffer, and the biofilm removal test was conducted in the same manner as in example 3 to measure the removal rate.

TABLE 4

|  | Example | | | | |
|---|---|---|---|---|---|
|  | 4-1 | 4-2 | 4-3 | 4-4 | 4-5 |
| Contact time with solution of iron (III) chloride (minute) | 1 | 5 | 10 | 30 | 120 |

TABLE 4-continued

|  |  |  |  | Example | | | | |
|---|---|---|---|---|---|---|---|---|
|  |  |  |  | 4-1 | 4-2 | 4-3 | 4-4 | 4-5 |
| Liquid composition | Concentration (ppm) | (a) | Hydrogen peroxide | 500 | 500 | 500 | 500 | 500 |
|  |  | (b) | Sodium ascorbate | 1000 | 1000 | 1000 | 1000 | 1000 |
|  | pH |  |  | 7.0 | 7.0 | 7.0 | 7.0 | 7.0 |
| Biofilm removal rate (%) |  |  |  | 28.1 | 34.6 | 40.0 | 52.6 | 68.8 |

Example 5

The biofilm removal test was conducted in the same manner as in example 2 by using a test piece on which the biofilm produced in example 2 was formed and liquid compositions to be brought into contact with a water system prepared by using components shown in Table 5. Here, the balance of each liquid composition was ultra-pure water, and the cleaning time was 60 minutes. The results are shown in Table 5.

TABLE 5

|  |  |  |  | Example | | | |
|---|---|---|---|---|---|---|---|
|  |  |  |  | 5-1 | 5-2 | 5-3 | 5-4 |
| Liquid composition | Concentration (ppm) | (a) | Sodium percarbonate | 1000 | 1000 | 1000 | 1000 |
|  |  | (b) | Ascorbic acid | 300 | 1000 | 3000 | 30000 |
|  |  | (c) | Tartaric acid | 1000 | 1000 | 1000 | 1000 |
|  | (a)/(b) (mass ratio) |  |  | 3.3 | 1 | 0.33 | 0.033 |
|  | pH |  |  | 4.2 | 4.1 | 4.0 | 4.0 |
| Biofilm removal rate (%) |  |  |  | 53.8 | 77.1 | 90.7 | 75.4 |

The invention claimed is:

1. A method for removing a biofilm containing a metal and formed in a water system, wherein the biofilm is brought into contact with
   (a) a compound having a hydroxyl radical generation ability (hereinafter also referred to as component (a)), and
   (b) a reducing agent (hereinafter also referred to as component (b)), wherein the components (a) and (b) are brought into contact with the biofilm together with (c) a monovalent or divalent organic acid or a salt thereof with a primary dissociation constant of 1.2 or more and 4.6 or less (hereinafter also referred to as component (c)), wherein the component (c) is one or more organic acids or salts thereof selected from malonic acid, 3-hydroxypropionic acid, succinic acid, lactic acid, tartaric acid, glycolic acid, maleic acid, fumaric acid, gluconic acid and salts thereof, and wherein the component (c) has a concentration of 50 ppm or more and 5000 ppm or less in the liquid composition.

2. The method for removing a biofilm according to claim 1, wherein the biofilm is brought into contact with a liquid composition containing the component (a), the component (b), the component (c) and water.

3. The method for removing a biofilm according to claim 2, wherein, in the liquid composition, the component (a) has a concentration of 50 ppm or more and 5000 ppm or less, and the component (b) has a concentration of 50 ppm or more and 50000 ppm or less.

4. The method for removing a biofilm according to claim 2, wherein, in the liquid composition, the component (a) has a concentration of 50 ppm or more and 5000 ppm or less, and the component (b) has a concentration of 50 ppm or more and 5000 ppm or less.

5. The method for removing a biofilm according to claim 1, wherein the components (a) and (b) are brought into contact with the biofilm at a pH of 2.0 or more and 10.0 or less.

6. The method for removing a biofilm according to claim 1, wherein the component (a) is one or more selected from hydrogen peroxide, percarbonate salts and organic peracids.

7. The method for removing a biofilm according to claim 1, wherein the component (b) is one or more selected from ascorbic acid or salts thereof, vitamin C extracted from natural products, tannic acid, erythorbic acid or salts thereof, N,N-diethylhydroxylamine, ascorbic acid derivatives or salts thereof, hydrosulfites, pyrosulfites, sulfites, hydrogensulfites, thiosulfates, thioureadioxide, gallic acid, methylhydroquinone, dimethylhydroquinone, trimethylhydroquinone, t-butylhydroquinone, methoxyhydroquinone and chlorohydroquinone.

8. The method for removing a biofilm according to claim 1, wherein the components (a) and (c) are brought into contact at a mass ratio of component (a)/component (c) of 0.01 or more and 100 or less.

9. The method for removing a biofilm according to claim 1, wherein the components (b) and (c) are brought into contact at a mass ratio of component (b)/component (c) of 0.01 or more and 100 or less.

10. The method for removing a biofilm according to claim 1, wherein the components (a) and (b) are brought into contact at a mass ratio of component (a)/component (b) of 0.01 or more and 100 or less.

11. The method for removing a biofilm according to claim 1, wherein the biofilm contains one or more metals selected from iron, manganese, nickel and copper.

12. The method for removing a biofilm according to claim 1, wherein the biofilm contains, per mg of the biofilm in a wet state, the metal in an amount of 0.5 ng or more and 50000 ng or less.

13. The method for removing a biofilm according to claim 1, wherein the water system is a cooling system comprising a water-cooled cooling tower.

14. The method for removing a biofilm according to claim 1, wherein the water system comprises a water flow path and/or a water storage tank.

15. A method for removing a biofilm containing a metal and formed in a water system, wherein the biofilm is brought into contact with a liquid composition containing (a) a compound having a hydroxyl radical generation ability (hereinafter also referred to as component (a)), (b) a reducing agent (hereinafter also referred to as component (b)), (c) a monovalent or divalent organic acid or a salt thereof with a primary dissociation constant of 1.2 or more and 4.6 or less (hereinafter also referred to as component (c)), and water, wherein the component (a) is one or more compounds selected from hydrogen peroxide and percarbonate salts, the component (b) is ascorbic acid or salts thereof, and the component (c) is one or more organic acids or salts thereof selected from malonic acid, 3-hydroxypropionic acid, succinic acid, lactic acid, tartaric acid, glycolic acid, maleic acid, fumaric acid, gluconic acid and salts thereof, wherein, in the liquid composition, the component (a) has a concentration of 80 ppm or more and 1000 ppm or less, and the component (b) has a concentration of 80 ppm or more and 1000 ppm or less, and wherein the components (a) and (b) are brought into contact with the biofilm at a pH of 3.5 or more and 10.0 or less.

16. The method for removing a biofilm according to claim 15, wherein the component (c) has a concentration of 80 ppm or more and 1000 ppm or less in the liquid composition.

\* \* \* \* \*